United States Patent [19]

Hiraoka

[11] Patent Number: 4,625,713
[45] Date of Patent: Dec. 2, 1986

[54] INSTRUMENT INCORPORATED IN A RESECTOSCOPE

[75] Inventor: Yasunori Hiraoka, Tokyo, Japan

[73] Assignee: Olympus Optical Co. Ltd., Tokyo, Japan

[21] Appl. No.: 561,109

[22] Filed: Dec. 13, 1983

[30] Foreign Application Priority Data

Dec. 14, 1982 [JP]  Japan ............................ 57-188675[U]

[51] Int. Cl.$^4$ ................................................ A61B 1/00
[52] U.S. Cl. .......................................... 128/4; 128/17
[58] Field of Search .................. 128/4, 5, 6, 7, 303.15, 128/303.17, 17

[56] References Cited

U.S. PATENT DOCUMENTS

| | | | |
|---|---|---|---|
| 2,031,020 | 2/1936 | Wappler | 128/303.15 |
| 4,030,502 | 6/1977 | Iglesias | 128/303.15 |
| 4,132,227 | 1/1979 | Ibe | 128/4 |
| 4,137,920 | 2/1979 | Bonnet | 128/7 |

Primary Examiner—Hugh R. Chamblee
Attorney, Agent, or Firm—Armstrong, Nikaido, Marmelstein & Kubovcik

[57] ABSTRACT

An extractor for extracting the prostatic endogland from the exogland is employed in a resectoscope comprising a outer sheath to be insertd into the urinary track, a slide member provided longitudinally slidably with respect to said sheath at the trailing end portion and a telescope to be inserted through forwards said slide member to the tip of sheath and inserted between the hypertrophied prostatic endogland and exogland to extract said endogland from the exogland.

8 Claims, 16 Drawing Figures

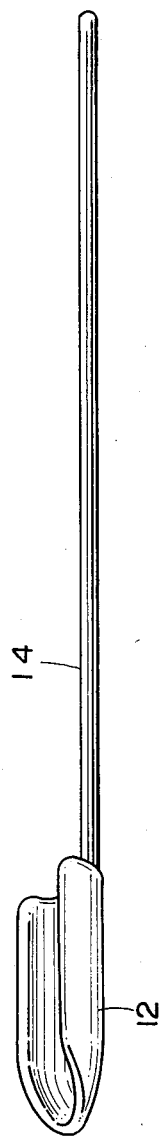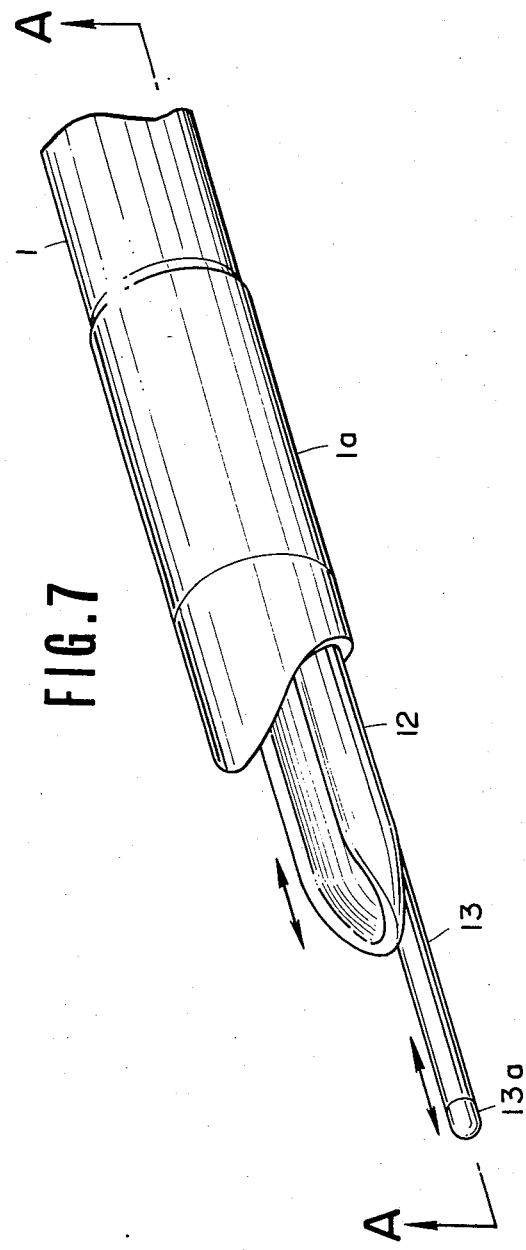

INSTRUMENT INCORPORATED IN A RESECTOSCOPE

FIELD OF THE INVENTION

The present invention relates to a prostatectoma employed together with an endoscope for the diagnosis and treatment of diseases of urinary track system such as urethra, urinary bladder, etc., i.e. resectoscope, especially employed for peeling and extracting the hypertrophied prostatic endogland caused by hyperplasia or the like from the exogland.

BACKGROUND OF THE INVENTION

The hypertrophied prostatic endgland has been cut and extracted by means of the fingers and instruments after the laparotomy. Such surgical treatment for cutting said prostatic endogland is accompanied with disadvantages such as prolonged period of recovery, etc. There has been developed a resectoscope as disclosed in U.S. Pat. No. 4,030,502 which makes the extraction of hypertrophied prostatic endogland through the urinary track without the laparotomy. Such extraction of prostatic endogland by means of such a resectoscope is carried out by cutting the prostatic endogland by means of a cutting loop which is extended and protruded from the tip of resectoscope and which passes a high frequency current therethrough under the observation of urinary bladder by means of a telescope attached to said resectoscope. However, the complete extraction of prostatic endogland by such prior art resectoscope is very difficult due to the serious danger on the human body and disadvantageous in that the residual endogland tissue may be again hypertrophied.

SUMMARY OF THE INVENTION

The present invention is directed to overcome the difficulty of complete extraction of prostatic endogland by the prior art resectoscope, namely only by means of the extracting loop extended and protruded from the tip of resectoscope. It is thus a principal object of the present invention to provide an instrument for extracting the prostatic endogland completely to eliminate the possibility recurring the hypertrophy of prostatic endogland.

It is another object of the present invention to provide an instrument incorporated into a resectoscope for extracting the prostatic endogland which can be inserted easily between the prostatic exogland and hypertrophied endogland under the direct observation by a telescope incorporated therein.

It is still another object of the present invention to provide an instrument for extracting the prostatic endogland which is incorporated into a resectscope and easily handled.

Other features and advantages achieved by the present invention will be apparent from the following disclosure.

SIMPLE DESCRIPTION OF THE DRAWINGS

Figure 2:
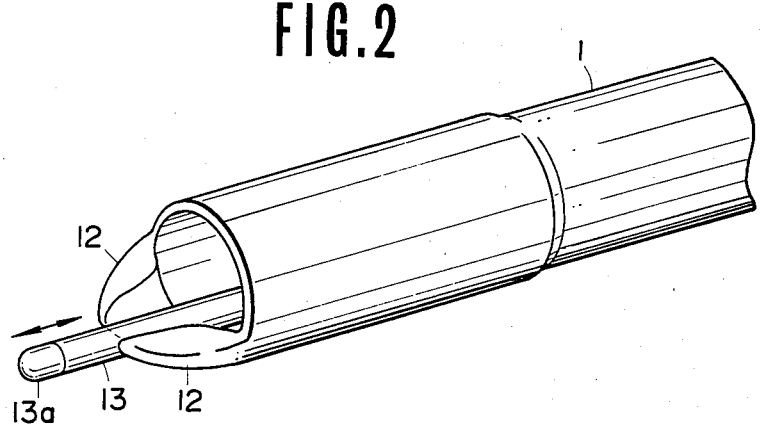
FIGS. 2 and 3 show a first embodiment of instrument for extracting the prostatic endogland incorporated in the resectoscope according to the present invention.
Figure 3:
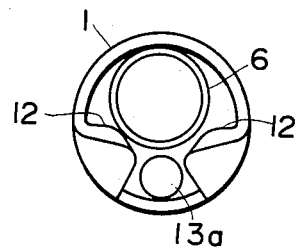

Wherein FIG. 2 is a perspective view of the tip portion.

Wherein FIG. 3 is a side view taken from the top portion as shown in FIG. 2.

Figure 4:
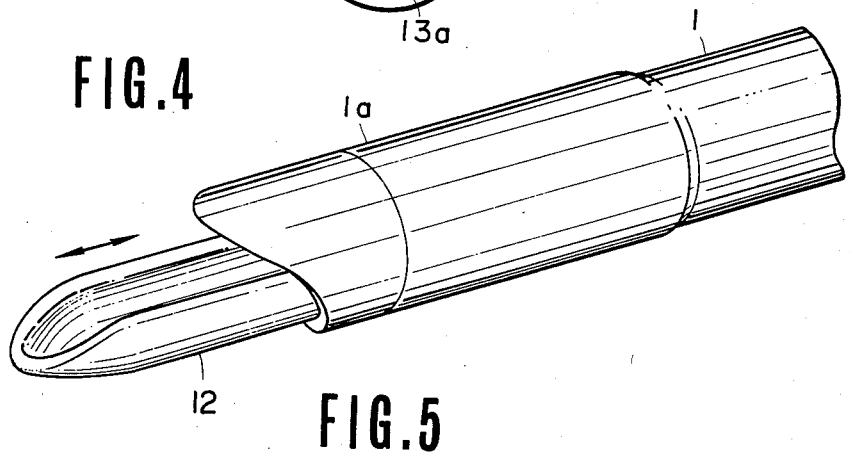
Figure 5:
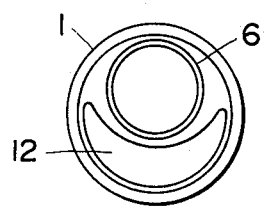

FIGS. 4 to 6 shows a second embodiment of the present invention.

Wherein FIG. 4 is a perspective view of the top portion.

Wherein FIG. 5 is a side view taken from the top portion of FIG. 4.

Wherein FIG. 6 is a perspective view showing the whole appearance of extracting element.

Figure 8:
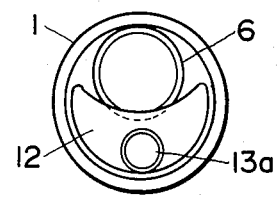
Figure 9:
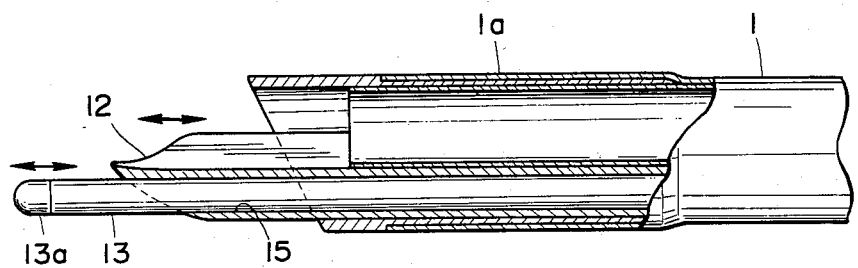

FIGS. 7 to 9 are a third embodiment of the present invention.

Wherein FIG. 7 is a perspective view of the top portion.

Wherein FIG. 8 is a side view taken from the top portion of FIG. 7.

Wherein FIG. 9 is a sectional view taken from line A—A in FIG. 7.

Figure 10:
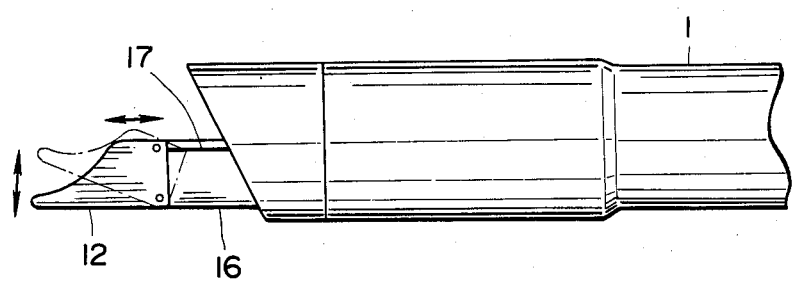

FIG. 10 is a front view of the top portion of a fourth embodiment of the present invention.

Figure 11:
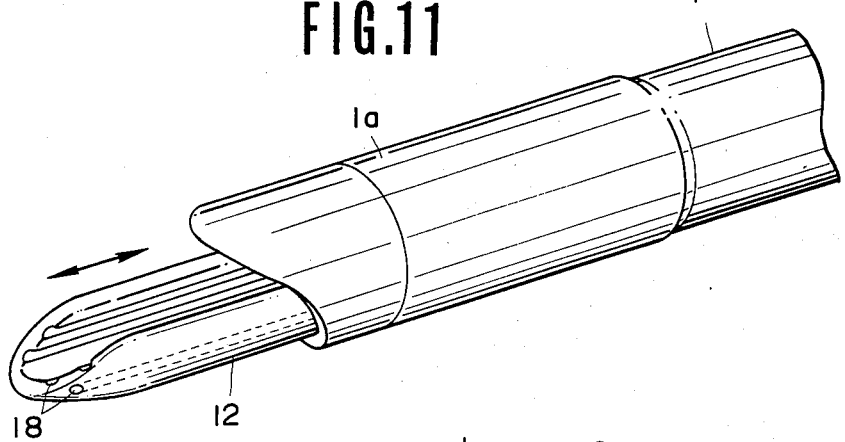
Figure 12:
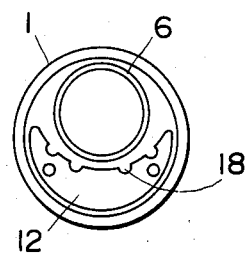

FIGS. 11 and 12 show a fifth embodiment of the present invention.

Wherein FIG. 11 is a perspective view of the top portion.

Wherein FIG. 12 is a side view taken from the top portion.

Figure 13:
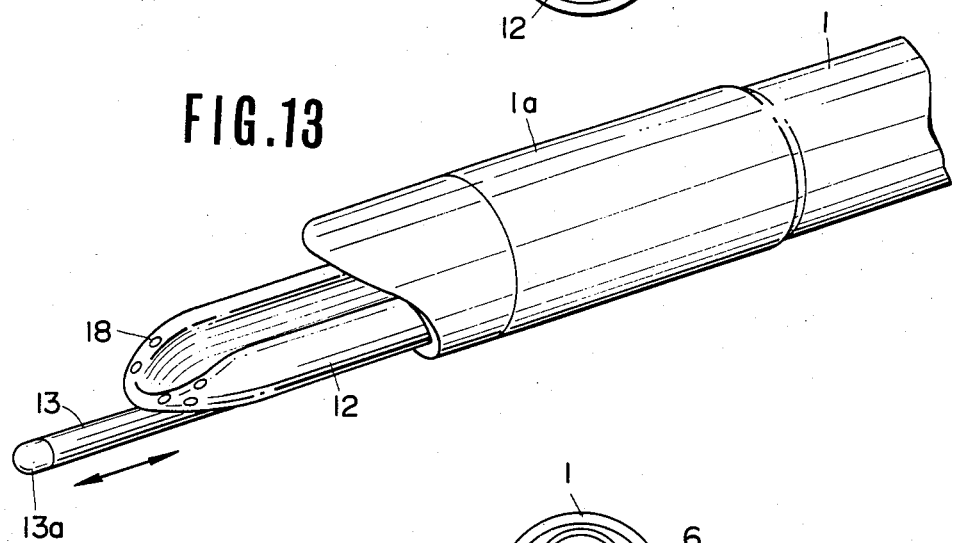
Figure 14:
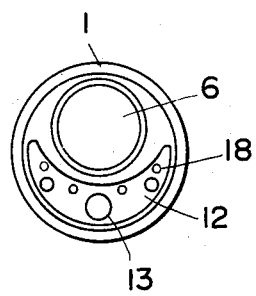

FIGS. 13 and 14 represent a sixth embodiment of the present invention.

Wherein FIG. 13 is a perspective view of the top portion.

Wherein FIG. 14 is a side view taken from the top of FIG. 13.

Figure 15:
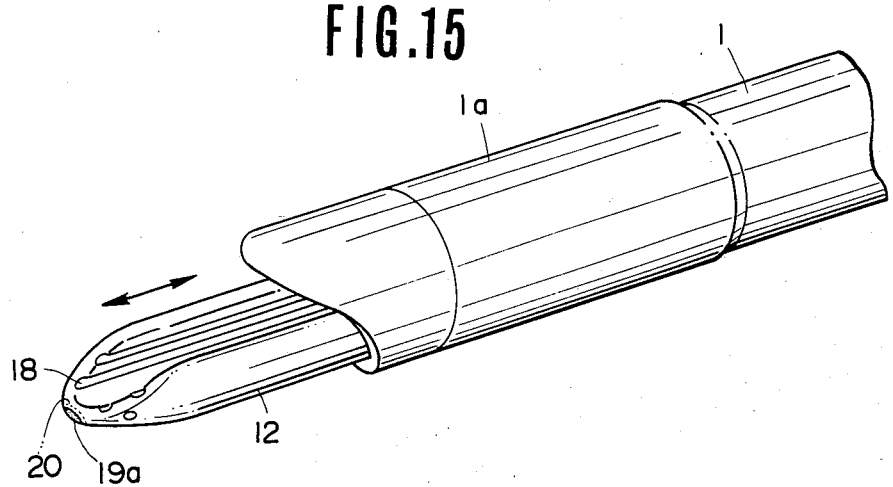
Figure 16:
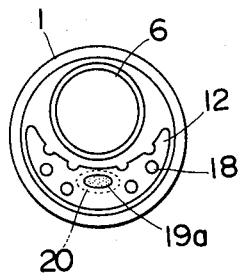

FIGS. 15 and 16 illustrate a seventh embodiment of the present invention.

Wherein FIG. 15 is a perspective view of the top portion.

Wherein FIG. 16 is a side view taken from the top of FIG. 15.

DESCRIPTION OF PREFERRED EMBODIMENTS ACCORDING TO THE INVENTION

Figure 1:
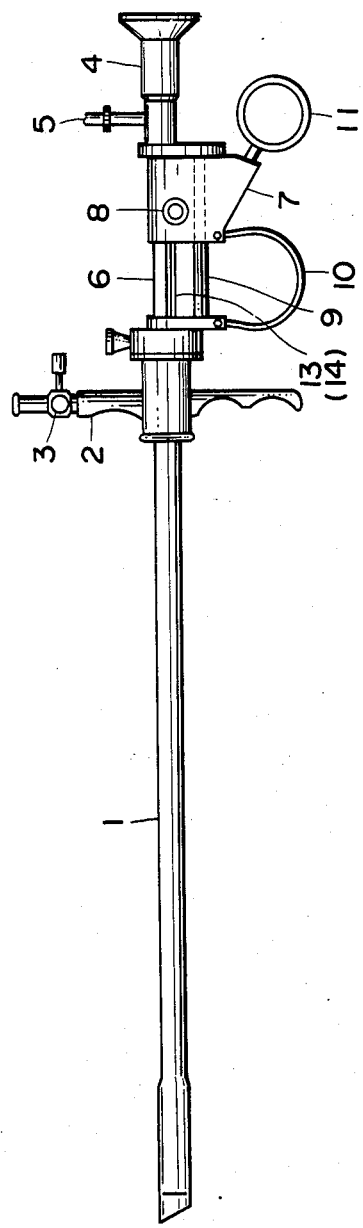
FIG. 1 is a general front view of the resectoscope.

FIG. 1 illustrates a general appearance of a resectoscope according to the present invention. Numeral 1 is a metal sheath having an outer diameter of, say, approximately 8 mm to be inserted through the urinary track. A protruded trigger 2 is provided with a water inlet 3 which is connected into the sheath 1 through said trigger 2 at the tip of said trigger. A telescope 6 having a diameter of, say, about 4 mm through the sheath 1 to the top portion of the resectoscope. The telescope 6 has an eye piece 4 and a connector 5 to a light source so as to observe directly the forward portion from the tip of said sheath 1 through the eye piece 4. A slide member 7 supported by a guide member 9 is attached longitudinally slidably along the guide member 9 at the handle of said sheath 1 and forced constantly backwards by means of a spring member 10 attached one end to said slide member 7 and another end to said handle of sheath 1. Said slide member 7 is provided with a extracting loop assembly, a terminal 8 for passing a high frequency current through a coagulation conductor as will be referred to hereinafter and a thimble 11. In addition, the slide member 7 is attached detachably extracting loop assembly to be inserted through the sheath 1 and base sides of extractor, coagulation conductor, etc. as will be referred to hereinafter so that the extraction loop, extractor, coagulation conductor, etc. can be protruded forwards from the tip of sheath 1 by displacing the slide member 7 forwards against the biased force of spring 10.

FIGS. 2 and 3 relate to a first embodiment of the instrument for extracting the prostatic endogland incorporated in the resectoscope according to the present invention wherein numeral 12 represents an extractor comprising two chisels which are protruded integrally or secured separately forwards from the lower portion of both sides at the tip of sheath 1. Said extractor 12 is made of metal or hard synthetic resin and composed so that said extractor 12 is inserted between the prostatic endogland and exogland to remove the endogland from the exogland. Hence the extractor 12 comprising two chisels has a shape to be inserted easily between the endogland and exogland and not to damage the protective membrane for the prostatic gland. Numeral 13 represents a tubular blood coagulation conductor having an electrode 13a and designed to be inserted into the sheath 1 and also inserted between the two chisels of the extractor 12 at the tip of the sheath. As shown in FIG. 1, the base portion of said coagulation conductor 13 is secured detachably to the slide member 7 and the coagulation conductor is designed to be energized by a high frequency current through the power terminal 8 at the fixation thereof. In addition, the tip electrode 13a of coagulation conductor 13 is designed to be protruded forwards beyond the extractor 12 by displacing said slide member 7 against the biased force of spring 10.

Such mechanism can extract the hypertrophied prostatic endogland from the exogland by inserting the extractor 12 comprising the two chisels and protruded from the tip of sheath 1 and the bleeding during the surgical operation can be stopped by means of the coagulation electrode 13a of the coagulation conductor 13.

FIGS. 4 to 6 relate to a second embodiment according to the present invention wherein the extractor 12 is formed separately from the sheath 1. The lower half inside wall of enlarged portion 1a of the sheath 1 is formed smoothly so that the extractor 12 shaped as a trough is slidable thereon and the tip of the enlarged portion 1a is formed into a convergent tongue so as to extract the prostatic endogland easily in cooperation with the extractor and not to damage the protective membrane of prostatic gland. The base portion of said extractor 12 is provided with, for example, a rod member 14, the end of said rod member 14 being attached detachably to the slide member 7 as shown in FIG. 1 so that the extractor 12 is protruded forwards from the tip of sheath 1 by displacing forwards said slide member 7.

FIGS. 7 to 9 related to a third embodiment according to the present invention wherein the extractor is formed approximately into a trough in a similar manner to the second embodiemnt but comprises a thick bottom recess and thin emerged but relatively dull tongue. The extractor is provided with a longitudinal through hole or through channel 15 at the thick bottom recess portion and through which the blood coagulation conductor 13 is inserted slidably longitudinally. The base portion of said extractor 12 is attached detachably to the slide member 7 as shown in FIG. 1 together with a rod connector or the like. The coagulation conductor 13 according to this embodiment is inserted into the through hole 15 and extended forwards through said slide member 7. The extractor 12 and coagulation conductor 13 are each independently protruded from the tip of sheath 1 and forwards from the tip of extractor 12 by forward displacement of the slide member 7 for the extractor 12 and by the displacement of a manipulator attached separately for the coagulation conductor 13.

FIG. 10 relates to a fourth embodiment according to the present invention. In this embodiment, the extractor has a form so that the trough of extractor as shown in the second embodiment is cut-down at the tip portion. The base portion comprising a rod end of the extractor 12 is connected longitudinally slidably to a connector member 16 secured to the slide member 7 as shown in FIG. 1. The lower portion of base portion of the extractor 12 is attached pivotally to the lower portion of said connector member 16 and the upper portion of base portion of the extractor 12 secures the end of wire cable 17 inserted through the connector member 16. Said wire cable 17 is extended to the handle portion (not shown) at the trailing end and pivotable vertically the extractor 12 at the fulcrum of pivot member by tightening or loosening the wire cable 17 by manipulating the handle portion.

FIGS. 11 and 12 related to a fifth embodiment according to the present invention. In this embodiment, the extractor 12 as shown in the second embodiment is provided a plurality of longitudinal through holes to define fluid irrigation holes and/or channels to improve the irrigation flow into (or from) the urinary bladder by means of the resectoscope to maintain the range of vision of telescope 6 under the favorable conditions.

FIGS. 13 and 14 relate to a sixth embodiment of the present invention wherein fluid irrigation holes and/or channels 18 are provided in a similar manner to the fifth embodiment through the extractor 12 in the third embodiment.

FIGS. 15 and 16 related to a seventh embodiment of the present invention wherein the extractor 12 and coagulation conductor are provided integrally. In these Figs., the extractor 12 is incorporated longitudinally with a blood coagulation conductor surrounded by an insulating layer 20 and the tip electrode 19a is secured to the tip of extractor 12. The fluid irrigation holes and/or channels 18 may be optionally provided through or on the extractor 12.

When the prostatic endogland is extracted from the exogland employing the extractor according to the present invention as referred to hereinabove, the major portion of hypertrophied prostatic endogland is cut by means of the cutting loop energized by a high frequency current in a manner similar to conventional operation under the direct observation of telescope incorporated in the resectoscope, the mucouse membrane of urinary track is cut at the end apart from the prostatic endogland by means of T.U.R. knife, the extractor 12 according to any embodiment is inserted through the cut-down membrane under the direct observation of telescope and the endogland is removed from the exogland. Said extractor 12 can be inserted easily between the prostatic endogland and exogland by displacing it forwards and backwards and can remove easily the endogland from the exogland. The bleeded portions of said cut-down membrane and extracted tissue can be coagulated easily by passing a high frequency current in abutment of the coagulation electrode 13a or 19a with the bleeded portion.

Various embodiments can be envisaged over a wide range without aparting from the spirit and scope of the present invention and based on the present invention. Accordingly, the present invention should not be limited to any particular embodiment except the limitation by the attached claims.

What is claimed is:

1. A combination of a resectoscope and an instrument for extracting a previous excised prostatic endogland; the resectoscope including an outer sheath to be inserted through the urinary tract, a slide member provided longitudinally slidably with respect to the sheath at a trailing end of the sheath, and a telescope inserted through the sheath to a tip end of the sheath for direct observation in front of the tip of the sheath; said instrument comprising an extractor having an extractor tip in the form of a tongue positioned adjacent said tip of said sheath for extracting the previous excised endogland from the exogland by inserting the tongue between the prostatic endogland and exogland.

2. The combination as claimed in claim 1, wherein said extractor is formed generally into a form of a trough slidable on the inner wall surface of a lower half of the tip of the sheath, the tip of said trough being formed as said extractor tip in the form of a tongue so as to remove the prostatic endogland from the exogland easily and not to damage the prostatic membrane; and wherein said extractor further comprises a base portion and a rod member longitudinal connected to said base portion, said rod member being detachably connected to said slide member so said extractor can be protruded forwards from the tip of the sheath by forward motion of said slide member.

3. The combination as claimed in claim 1, wherein said extractor tip comprises two chisels protruded forwards from both lower sides of the tip of the sheath.

4. The combination as claimed in claim 1, wherein said extractor tip is upwards pivotally mounted; and said extractor further comprises means connected to said extractor tip for pivoting said extractor tip.

5. The combination as claimed in claim 1, wherein said instrument further comprises a blood coagulation conductor having an electrode adjacent the tip of the sheath, said conductor being inserted longitudinally extendably and retractably in the sheath so as to be protruded from the tip of the sheath by manipulation of a handle at a base portion of the resectoscope.

6. The combination as claimed in claim 1, wherein said extractor is formed generally in the form of a dull trough comprising a thick bottom recess and a thin tip, said thick bottom recess being provided with a longitudinal through hole and/or channel; said instrument further comprises a blood coagulation conductor provided with an electrode at a tip thereof, said conductor being extendably and retractably inserted in said longitudinal through hole and/or channel; and said extractor and said conductor are adapted to be protruded independently from the tip of the sheath by manipulation of a handle at a base portion of the resectoscope.

7. The combination as claimed in claim 1, wherein said instrument further comprises a blood coagulation conductor incorporated in said extractor and having an electrode secured in said extractor tip.

8. The combination as claimed in claim 2, wherein said extractor has a plurality of irrigation fluid through holes formed therein.

* * * * *